United States Patent [19]

Yukawa et al.

[11] Patent Number: 4,610,827

[45] Date of Patent: Sep. 9, 1986

[54] AMINO ACID COMPLEX AND A METHOD FOR OPTICAL RESOLUTION OF A DL-AMINO ACID

[75] Inventors: Toshihide Yukawa, Yokohama; Toru Ikeda; Shinichi Kishimoto, both of Yokkaichi; Katsumi Sugiyama, Yokosuka, all of Japan

[73] Assignee: Ajinomoto Co., Inc., Tokyo, Japan

[21] Appl. No.: 629,468

[22] Filed: Jul. 10, 1984

[30] Foreign Application Priority Data

Jul. 22, 1983 [JP] Japan .................... 58-133991

[51] Int. Cl.$^4$ ............... C07C 103/50; C07B 57/00
[52] U.S. Cl. ............... 260/501.11; 548/496; 548/498; 562/401
[58] Field of Search .............. 260/501.11; 562/401; 548/496, 498

[56] References Cited

U.S. PATENT DOCUMENTS

| | | | |
|---|---|---|---|
| 3,991,077 | 11/1976 | Uzuki et al. | 562/401 |
| 4,198,524 | 4/1980 | Tashiro et al. | 562/401 |
| 4,224,239 | 9/1980 | Tashiro et al. | 562/401 |
| 4,411,840 | 10/1983 | Bethge et al. | 562/401 |

*Primary Examiner*—Natalie Trousof
*Assistant Examiner*—Vera C. Clarke
*Attorney, Agent, or Firm*—Oblon, Fisher, Spivak, McClelland & Maier

[57] ABSTRACT

A method for optical resolution of a DL-amino acid comprising reacting the DL-amino acid with an optically active N-acyl aspartic acid in a solvent or mixture of solvents, and separating the resulting two diastereomeric salts by way of the difference between their solubilities in the solvent or mixture of solvents. The difference in solubility may be enhanced by cooling, concentration, addition of a solubility-decreasing organic solvent, pH adjustment or salting out.

5 Claims, No Drawings

AMINO ACID COMPLEX AND A METHOD FOR OPTICAL RESOLUTION OF A DL-AMINO ACID

DESCRIPTION OF THE INVENTION

This invention relates to an amino acid complex and a method for optical resolution of a DL-amino acid, and more particularly to a method comprising reacting an optically active N-acyl aspartic acid as the resolving agent with a DL-amino acid in a solvent, and optically resolving the DL-amino acid by means of the difference in solubility between the resulting two types of complexes (diastereomers). This invention also relates to an amino acid complex of an optically active amino acid and an optically active N-acyl aspartic acid which is useful in such method and which is obtained as an intermediate in the same method.

An optically active amino acid is a substance very useful as a starting material for the production of pharmaceuticals, sweeteners and the like. However, an amino acid obtained by synthesis is a racemate (DL-form) and should be optically resolved.

The conventional methods for resolving a DL-amino acid include the following:

(1) asymmetric hydrolysis of an N-acyl-form by acylase (Japanese Patent Application tokkaisho 51-110095)

(2) direct resolution by inoculation of either the DL-amino acid itself or after converting it to a salt (Japanese Patent Application tokkosho 52-8821)

However, the enzymatic method mentioned in (1) is disadvantageous since it involves acylation of the DL-amino acid and requires the use of an expensive enzyme. As for the resolution by inoculation in (2), it has disadvantages such as low resolution yields and the need for large-scale equipment if it is to be performed on a commercial basis.

After devoted research for developing commercially advantageous methods for optical resolution of DL-amino acids, the present inventors have discovered that a DL-amino acid can be very effectively resolved in the presence of an optically active N-acyl aspartic acid as a resolving agent. This finding has become the basis for the accomplishment of this invention.

According to the method of this invention, a DL-amino acid is reacted with an optically active N-acyl aspartic acid in a solvent to produce two diastereomers, i.e., optically active N-acyl aspartic salts of D- and L-amino acids. Using the difference in solubility between the two diastereomers, only one salt is separated by crystallization (i.e., optically resolved), and thereafter, the desired optically active amino acid is obtained by a suitable technique such as alkali treatment. The method of the present invention enables the desired optically active amino acid to be produced easily and in a highly pure form, and hence can be implemented commercially with great advantages.

The optically active N-acyl aspartic acid used as a resolving agent in the method according to this invention is desirably of a type which reacts with the starting DL-amino acid to produce two diastereomers which differ greatly in solubility. Specific examples are N-carbobenzoxyaspartic acid, N-benzenesulfonylaspartic acid, N-acetylaspartic acid, N-toluenesulfonylaspartic acid, N-benzoylaspartic acid. These compounds are well known and can be easily produced by known methods.

The amino acids which are to be optically resolved by the present invention are not limited to particular compounds, and some examples are phenylalanine, valine, leucine, alanine, phenylglycine, substituted phenylglycines, methionine, norvaline, lysine and tryptophane.

Suitable solvents are water, hydrophilic organic solvents (e.g., alcohols such as methanol, ethanol, isopropyl alcohol and N,N-dimethylformamide) and mixtures thereof.

Reaction temperatures not higher than the boiling point of the solvent are acceptable, but typical temperatures range from −20° C. to 100° C., and the preferred temperatures are within the range of from 0° C. to 80° C. Crystallization temperatures are desirably not higher than 60° C. so that the undesirable antipodal chiral amino acid or its complex will not crystallize during solid-liquid separation.

In order to produce the desired complex, the method of the present invention is preferably performed at a pH in the range of 1 to 4, but an optimum pH range may vary depending upon the type of the amino acid to be resolved and depending on whether amino acid salts are present in the reaction system.

The amount of the optically active N-acyl aspartic acid employed as a resolving agent in this method may range from 0.4 to 4 mols per mol of the DL-amino acid. Salts of the DL-amino acid to be optically resolved, such as sulfates, hydrochlorides, phosphates, sodium salts, potassium salts and the like, are sometimes employed during the resolution. These salts help solubility in solution of (a) the enantiomer (e.g., D-phenylalanine) of the amino acid which is a component of the intended diastereomer (,e.g., N-carbobenzoxy-L-aspartic acid/L-phenylalanine) or (b) a diastereomer comprising said enantiomer (e.g., N-carbobenzoxy-L-aspartic acid/D-phenylalanine), thereby to contributing to an increase in resolution yields.

An example embodiment of this invention wherein two diastereomers, i.e., optically active N-acyl aspartic acid salts of the respective D- and L-amino acids; are separated by means of the difference in their solubility follows:

A solution containing a mixture of a DL-amino acid and an optically active N-acyl aspartic acid is prepared, optionally in the presence of salts of the amino acid. This solution is treated by cooling, concentration, salting out, addition of a solubility decreasing organic solvent and/or by pH adjustment, so that only a diastereomer of the lower solubility may crystallize as a solid phase, followed by a solid-liquid separation in a suitable manner to separate the crystallized solid phase. The amino acid to be optically resolved is not necessarily an equimolar mixture of D- and L-forms.

The complex of an optically active amino acid and an optically active N-acyl aspartic acid which has been isolated in the form of a crystal may be easily optically purified as desired by, for example, recrystallization from water or an aqueous medium.

After thus obtaining the intended diastereomer, an appropriate method may be utilized for the isolation of the desired optically active amino acid, for the recovery of an N-acyl aspartic acid, or for the recycling of this acid. One example of such method is as follows:

The complex of an optically active amino acid and an optically active N-acyl aspartic acid is suspended in water or an aqueous medium; an alkali such as sodium hydroxide, potassium hydroxide, sodium carbonate and the like is added to decompose the complex, thereby to crystallizing only the desired optically active amino acid for separation; the optically active N-acyl aspartic acid contained in the mother liquor may be recycled for another use as a source of the optically resolving agent, either as it is or after pH adjustment.

Alternatively, the complex of an optically active amino acid and an optically active N-acyl aspartic acid is dissolved in an acidic solution such as a diluted aqueous solution of sulfuric acid or hydrochloric acid. The resulting solution is passed through an ion exchange resin column, an eluant made of an alkaline solution such as an aqueous solution of ammonia or sodium hydroxide is passed through this column, and a solution of the optically active aspartic acid and a solution of the desired optically active amino acid are obtained respectively as a breakthrough solution and as an effluent.

The melting points and solubilities of some of the diastereomers obtained according to this invention are shown in Table 1.

TABLE 1

| Amino acid salts of N—acyl aspartic acids (*1) | Melting point (°C.) | Water solubility (*2) |
| --- | --- | --- |
| N—carbobenzoxy-L-aspartic acid/ L-phenylalanine | 163 | 1.2 |
| N—carbobenzoxy-L-aspartic acid/ D-phenylalanine | 159 | 4.0 |
| N—benzenesulfonyl-L-aspartic acid/ L-phenylalanine | 171 | 2.1 |
| N—benzenesulfonyl-L-aspartic acid/ D-phenylalanine | 205 (decomposed) | 3.7 |

(*1) The molar ratio of N—substituted-L-aspartic acid and an optically active amino acid is 1:1 for all of the salts.
(*2) The weight in grams of an amino acid contained in 100 ml of a saturated solution at 40° C.

The molar ratio of an optically active amino acid to an optically active N-acyl aspartic acid in their complex is not necessarily 1:1. For example, a complex of L-phenylalanine and N-carbobenzoxy-L-aspartic acid may form a mixed crystal, and the molar ratio of the amino acid to the aspartic acid ranges from 1:1 to 1:2 depending on the crystallization conditions. Some complexes will be dehydrated and others will not. However, regardless of these differences in the composition of the complexes, the optical resolution according to this invention is carried out as intended, and the desired optically active amino acid may be eventually obtained from the complex.

Further, when an optically active amino acid is crystallized in the form of an amino acid complex according to this invention, not only enantiomers (optical impurities) but also other impurities may be eliminated. For example, an optically active N-acyl aspartic acid is added to a solution of a DL-amino acid containing colored impurities, and than a diastereomer having the lower solubility is crystallized for separation. In this way, an amino acid complex free from the colored impurities is obtained, and an optically active amino acid free from the colored impurities may be eventually produced. Alternatively, an optically active N-acyl aspartic acid which forms a diastereomer of the lower solubility is added to a solution of an optically active amino acid containing colored impurities, and the resulting crystal of an amino acid complex is separated thus obtaining an optically active amino acid free from any colored impurities.

This invention will now be further described by referring to examples, but it will be understood that these examples should not be interpreted as limiting the scope of this invention in any way.

In the examples, the diastereomeric salts obtained were dissolved in an aqueous solution of hydrochloric acid, and the resulting solution was passed through a cation exchange column for absorption of the amino acid. An aqueous solution of ammonia was passed through the column, and the resulting effluent was concentrated to dryness for isolation of the amino acid, and its optical purity was analyzed by measuring the optical rotation thereof.

EXAMPLE 1

Eight grams of DL-phenylalanine, 10 g of N-carbobenzoxy-L-aspartic acid and 2.4 g of sulfuric acid were dissolved in 90 ml of water. A 10% aqueous solution (9.7 ml) of caustic soda was added to the resulting solution over six hours while it was continuously stirred at 50° C. As a result, half of the sulfuric acid was neutralized, and the molar amount of the remaining sulfuric acid was a quarter of the amount of DL-phenylalanine. (It will be noted that in the other examples also, the amount of sulfuric acid was adjusted to be one mol per 2 mols of the finally present D-phenylalanine.) The resulting crystal was separated, washed with 10 ml of water and dried to give 8.2 g of L-phenylalanine/N-carbobenzoxy-L-aspartic acid salt. An analysis revealed that the optical purity of the L-phenylalanine contained in this salt was 98%. The molar ratio of L-phenylalanine to N-carbobenzoxy-L-aspartic acid contained in this salt was 1:1.5. An X-ray diffraction pattern of this salt in powder form had peaks at $2\theta=4$, 16.2, 17.4, 17.6, 18.6, 19.1, 24.6 and 28.8 (degrees).

This crystal was suspended in 30 ml of water, and was cooled to 5° C. after adjustment of pH 7 by caustic soda. The resulting crystal was separated and dried to give 1.8 g of L-phenylalanine. An analysis showed that the optical purity of this amino acid was at least 98%.

EXAMPLE 2

Eight grams of DL-phenylalanine, 8.1 g of N-carbobenzoxy-L-aspartic acid and 1.2 g of sulfuric acid were added to 100 ml of water and the resulting solution was heated to 60° C. This solution was cooled to 40° C. at a rate of 2° C. per hour while stirring, and was stirred for another two hours. The resulting crystal was separated, washed in 20 ml of water and dried to give 8.2 g of an L-phenylalanine/N-carbobenzoxy-L-aspartic acid salt. Analysis of this salt revealed that the optical purity of the L-phenylalanine was 97%.

This crystal was suspended in 30 ml of water, and was cooled to 5° C. after pH adjustment to pH 7 by caustic soda. The resulting crystal was separated and dried to obtain 2.2 g of L-phenylalanine. Analysis showed an optical purity of at least 98%.

EXAMPLE 3

Eight grams of DL-phenylalanine and 1.2 g of sulfuric acid was suspended in 100 ml of water at 40° C. Ten grams of N-carbobenzoxy-D-aspartic acid was added to the solution over five hours, while this solution was continuously stirred. The resulting crystal was separated, washed with 10 ml of water and dried to give 5.2 g of a D-phenylalanine N-carbobenzoxy-D-aspartic acid. Analysis revealed that the optical purity of the D-phenylalnine was 98%.

This crystal was suspended in 30 ml of water, and was cooled to 5° C. after adjustment to pH 7 by caustic soda.

The obtained crystal was separated and dried to give 1.4 g of D-phenylalanine. Analysis showed that its optical purity was at least 98%.

EXAMPLE 4

Six grams of DL-phenylalanine, 5.4 g of N-benzenesulfonyl-L-aspartic acid and 1.8 g of sulfuric acid were dissolved in 110 ml of water. While this solution was continuously stirred at 50° C., a 10% aqueous solution of caustic soda (7.3 ml) was added over five hours. The resulting crystal was separated, washed with 10 ml of water and dried to give 3.1 g of an L-phenylalanine/N-benzenesulfonyl-L-aspartic acid salt. Analysis of this salt revealed that the optical purity of the L-phenylalanine was 94%.

EXAMPLE 5

A 11.7 g portion of DL-valine, 13.4 g of N-carbobenzoxy-L-aspartic acid and 2.5 g of sulfuric acid were added to 50 ml of water and the resulting solution was heated to 50° C. This solution was cooled to 20° C. at a rate of 2° C. per hour while stirring, and was stirred for another two hours. The resulting crystal was separated, washed with 20 ml of water and dried to give 9.7 g of an L-valine/N-carbobenzoxy-L-aspartic acid salt. Analysis showed that the optical purity of the L-valine was 98%.

This crystal was suspended in 20 ml of water, and was cooled to 5° C. after pH adjustment to pH 7 by caustic soda. The resulting crystal was separated and dried to give 1.7 g of L-valine. Analysis revealed that the optical purity of this acid was at least 98%.

EXAMPLE 6

Ten grams of DL-leucine, 12.2 g of N-carbobenzoxy-L-aspartic acid and 1.9 g of sulfuric acid were added to 500 ml of water and the resulting solution was heated to 60° C. This solution was cooled to 10° C. at a rate of 2° C. per hour while stirring, and was stirred for another two hours. The resulting crystal was separated, washed with 30 ml of water and dried to give 9.1 g of an L-leucine/N-carbobenzoxy-L-aspartic acid. Analysis showed that the optical purity of the L-leucine was 95%.

EXAMPLE 7

A solution having 0.2 g of D-phenylalanine, 2.3 g of L-phenylalanine and 4.0 g of N-carbobenzoxy-L-aspartic acid dissolved in 80 ml of water was prepared at 60° C. This solution was left to stand for three days at about 10° C., and the resulting crystal was separated and washed with about 10 ml of water to give 7.6 g of a product with a moisture content of about 30%. Analysis revealed that the optical purity of the L-phenylalanine contained in the product was 98%.

An X-ray diffraction pattern of this crystal in powder form had peaks at $2\theta = 5$, 17.7, 18.7 and 28.2 (degrees). It was confirmed that this crystal consists of an equimolar mixture of L-phenylalanine, N-carbobenzoxy-L-aspartic acid and water.

This crystal was suspended in 30 ml of water and cooled to 5° C. after pH adjustment to pH 7 by caustic soda. The resulting crystal was separated and dried to give 2.0 g of L-phenylalanine. An analysis revealed that the crystal had an optical purity of at least 99%.

What is claimed is:

1. A complex of an optically active amino acid and an optically active N-acyl aspartic acid.

2. The complex as defined in claim 1, wherein the acyl group is either a carbobenzoxy group or a benzenesulfonyl group.

3. A method for optical resolution of a DL-amino acid comprising reacting the DL-amino acid and an optically active N-acyl aspartic acid in a solvent or a solvent mixture, and separating the resulting two types of diastereomers by means of the difference between their solubilities in said solvent or said solvent mixture.

4. A method for optical resolution as defined in claim 3, wherein the acyl group of the optically active N-acyl aspartic acid is either a carbobenzoxy group or a benzenesulfonyl group.

5. The method of claim 3 wherein the difference in solubility between said diastereomers is enhanced by one or more of the following treatments: cooling, concentration, addition of a solubility decreasing organic solvent and pH adjustment.

* * * * *